(12) United States Patent
Kabir et al.

(10) Patent No.: US 8,378,139 B2
(45) Date of Patent: Feb. 19, 2013

(54) CONTINUOUS OLIGOMERIZATION OF ISOCYANATES

(75) Inventors: Hocine Kabir, Serezin du Rhone (FR); Johannes Schwarz, Lyon (FR); Christophe Gourdon, Toulouse (FR); Sébastien Elgue, Baziege (FR)

(73) Assignees: Centre National de la Recherche Scientifique (C.N.R.S.), Paris (FR); Institut National Polytechnique de Toulouse, Toulouse (FR); Perstorp France, Saint-Priest (FR)

( * ) Notice: Subject to any disclaimer, the term of this patent is extended or adjusted under 35 U.S.C. 154(b) by 0 days.

(21) Appl. No.: 12/936,342

(22) PCT Filed: Apr. 2, 2009

(86) PCT No.: PCT/FR2009/050562
§ 371 (c)(1), (2), (4) Date: May 31, 2011

(87) PCT Pub. No.: WO2009/136032
PCT Pub. Date: Nov. 12, 2009

(65) Prior Publication Data
US 2011/0218314 A1 Sep. 8, 2011

(30) Foreign Application Priority Data
Apr. 3, 2008 (FR) .................................... 08 52233

(51) Int. Cl.
*C07C 263/00* (2006.01)

(52) U.S. Cl. .......... 560/345; 560/25; 560/115; 560/158; 560/336; 560/355; 564/44; 564/45

(58) Field of Classification Search ................ 560/336, 560/355, 345, 26, 115, 158; 564/44, 45
See application file for complete search history.

(56) References Cited

U.S. PATENT DOCUMENTS
6,093,817 A * 7/2000 Kohlstruk et al. ............ 544/193
6,642,382 B2 11/2003 Bernard et al.
2009/0292098 A1 11/2009 Wagner et al.

FOREIGN PATENT DOCUMENTS
FR 2804112 A1 7/2001
WO WO 2006/063745 A1 6/2006
WO WO 2006063745 A1 * 6/2006

OTHER PUBLICATIONS
International Search Report for corresponding PCT//FR2009/050562 dated Oct. 2, 2009 (4 pages).

* cited by examiner

*Primary Examiner* — Michael L Leonard
(74) *Attorney, Agent, or Firm* — Buchanan Ingersoll & Rooney PC (57) ABSTRACT

A process for oligomerizing isocyanates includes a step of continuous conversion of an isocyanate monomer into polyisocyanate containing carbamate and/or allophanate groups, in the presence of a catalyst, wherein the conversion step is carried out in a reactor having a specific heat exchange coefficient of greater than or equal to approximately 200 kW/m$^3$/° C.

12 Claims, 4 Drawing Sheets

CONTINUOUS OLIGOMERIZATION OF ISOCYANATES

CROSS-REFERENCE TO PRIOR APPLICATIONS

This application claims priority under 35 U.S.C. §119 of FR 0852233, filed Apr. 3, 2008, and is a 35 U.S.C. §371 national stage application of PCT/FR 2009/050562, filed Apr. 2, 2009 and designating the United States (published in the French language on Nov. 12, 2009, as WO 2009/136032 A1; the title and abstract were also published in English), each hereby expressly incorporated by reference in its entirety and each assigned to the assignee hereof.

The object of the present invention is a method for continuous oligomerization of isocyanates.

Many methods for preparing polyisocyanates are known and comprise the use of various catalysts.

Thus, patent application EP 0 003 765 describes partial cyclotrimerization of isophorone diisocyanate (IPDI or 1-isocyanato-3,3,5-trimethyl-5-isocyanatomethyl-cyclohexane), via the application of a discontinuous method (or batch method), using a hydroxide of a quaternary hydroxyalkylammonium as a catalyst.

Patent application DE 10 2004 060 131 describes a method for continuous preparation of polyisocyanates comprising the use of a catalyst notably selected from quaternary ammonium salts. It is specified that the temperature in the reactor varies from 40° C. to 110° C., but this temperature is not uniform inside the reactor because of the existence of various temperature areas in said reactor (preheating, reaction and cooling areas). Finally, this document only mentions the use of a tubular reactor.

Patent application EP 0 927 731 describes a method for continuous preparation of a polyisocyanate from IPDI in the presence of quaternary ammonium hydroxide or carboxylate, and at a temperature from 40 to 120° C., but this temperature is not uniform inside the reactor because of the existence of various temperature areas in said reactor (preheating, reaction and cooling area). Finally, this document relates to the use of a tubular reactor.

Generally, catalysts notably based on a quaternary ammonium hydroxide such as choline have very strong reactivity, which makes the control of the trimerization reaction difficult, in particular when the starting isocyanate is an aliphatic isocyanate.

Thus, the use of very active catalysts of this type requires control of the temperature inside the reactor.

The object of the present invention is to provide a novel method for preparing polyisocyanates by using, as catalysts, catalysts with very strong reactivity, notably quaternary ammonium hydroxides such as choline, easy to apply in spite of the very strong reactivity of the catalysts used.

The object of the present invention is also to provide such a method during which the temperature inside the reactor used is controlled.

The object of the present invention is also to provide a novel method for preparing polyisocyanates by using as catalysts, catalysts with very strong reactivity, notably quaternary ammonium hydroxides such as choline, in a reactor allowing removal of the heat of the reaction.

The object of the present invention is also to provide such a method allowing simultaneous addition of the catalyst and of the isocyanate monomer.

The present invention relates to a method for oligomerizing isocyanates comprising a step for continuously converting an isocyanate monomer into a polyisocyanate containing carbamate and/or allophanate groups in the presence of a catalyst, in which the conversion step is carried out in a reactor, the specific heat exchange coefficient of which is greater than or equal to about 200 kW/m$^3$/° C., and is preferably of about 500 kW/m$^3$/° C. to about 4 000 kW/m$^3$/° C.

The method of the invention is therefore characterized by its continuous nature and by maintaining the temperature in the reactor in a given range. With the method of the invention, it is thereby possible to maintain all along the reaction a constant and controlled temperature inside the reactor by efficient and controlled transfer of the calories.

Advantageously, the reactor used within the scope of the present invention has a specific heat exchange coefficient from about 200 kW/m$^3$/° C. to about 14 000 kW/m$^3$/° C.

The method according to the invention is characterized in that the aforementioned conversion step is advantageously carried out continuously in a reactor maintained at a temperature from about 65° C. to about 180° C., notably from about 65° C. to about 130° C., preferably from about 80° C. to about 100° C., and more particularly at a temperature from about 90° C. to about 95° C.

Thus, applying a continuous method allows better control of the reaction as compared with the application of a discontinuous method (batch method) as well as control of the conversion rate.

With this application of the continuous method it is also possible to reduce the volume of the equipment used and to obtain a gain in productivity. Moreover, the continuous method increases safety in conducting the latter.

The reactors used within the scope of the present invention have a smaller volume as compared with the reactors used in batch methods.

Thus, in the case of a drift of the process, as the engaged reaction volume is much smaller, managing the method in terms of safety is easier.

With the method of the present invention it is possible to modulate and to control the conversion rate. By controlling the conversion rate and more particularly by maintaining it, it is possible to control the physico-chemical properties of the obtained product (trimer), such as the viscosity or the NCO function level.

The term of oligomerization designates a process for transforming a monomer, or a mixture of monomers into an oligomer, which is a substance consisting of molecules of intermediate molecular mass essentially formed by the repetition of a small number of atoms or atom groups, called «constitutive units» and deriving from low molecular mass molecules.

The specific heat exchange coefficient is designated by US/V, wherein U represents the heat exchange coefficient, S represents the surface area of the reactor and V represents the volume of the reactor.

The coefficient U is related to the heat conductivity of the material of the reactor and therefore to the nature of material of the reactor, as well as to the type of method applied, i.e. for example depending on the stirring and turbulence of the fluids or on the nature of the fluids used.

The heat exchange coefficient U between two fluids 'a' and 'b' on either side of a plate of thickness 'e' is defined as the sum of the heat transfer resistances such that: $1/U = 1/h_a + e/\lambda + 1/h_b$, $h_a$ and $h_b$ representing the convection resistances of each of the fluids and $\lambda$ the heat conductivity of the material separating them.

By designating $\Delta T_a = (T_a)^e - (T_a)^s$ and $\Delta T_b = (T_b)^e - (T_b)^s$ as respectively the temperature change between the inlet and the outlet of the hot fluid and of the cold fluid, the average logarithmic temperature is defined by:

$$\Delta T_m I = (\Delta T_a - \Delta T_b)/\text{Ln}\,[((T_a)^e - (T_b)^e)/((T_a)^s - (T_b)^s)]$$

The energy or heat flow, ($\phi$), transferred from the hot fluid 'a' to the cold fluid 'b' is then expressed by: $\phi = US\,\Delta T_m I$ This transferred energy corresponds:
to the energy provided by the hot fluid and which cools by $\Delta T_a$:
$W = Q_a Cp_a \Delta T_a$
to the energy received by the cold fluid and which heats up by $\Delta T_b$:
$W = -Q_b Cp_b \Delta T_b$,
Q and Cp respectively being the heat flow and heat capacity of the fluids crossing the process.

The energy conservation balance leads to the following conservation relationships $$\phi = US\Delta T_m I = Q_a CP_a \Delta T_a = -Q_b CP_b \Delta T_b$$

The measurements of the temperatures of both fluids at the inlet and at the outlet of the process and the exchange surface area S therefore allow measurement of the heat exchange coefficient U, a characteristic of the system.

Thus, the heat transfer coefficient is calculated as indicated below, in a case when the cold fluid (or 'utility' fluid) and the hot fluid (or 'process' fluid) which is intended to be cooled, are both water.

The experiment is conducted on two plates: a 'utility' plate which receives the cold fluid and a 'process' plate which receives the hot fluid. Both plates are sealably joined so as to allow heat transfer from the hot fluid to the cold fluid. The 'utility' fluid is sent into the 'utility' plate at a flow rate of $Q_b = 0.02867$ kg/s and at an inlet temperature of $(T_b)^e = 9.8°$ C. The 'process' fluid is sent into the 'process' plate at a flow rate of $Q_a = 0.00213$ kg/s and at an inlet temperature $(T_a)^e = 69.6°$ C. The temperature of the 'utility' fluid at the outlet of the 'utility' plate is measured as $(T_b)^s = 11.5°$ C. The temperature of the 'process' fluid at the outlet of the 'process' plate is measured as $(T_a)^s = 46°$ C. The change in temperature of the 'utility' fluid is therefore $\Delta T_b = -1.7°$ C. The change in temperature of the 'process' fluid is therefore $\Delta T_a = 23.6°$ C. The average heat capacity of the 'utility' fluid between the inlet and the outlet of the 'utility' plate is equal to $Cp_b = 4201$ J/kg/° C. The average heat capacity of the 'process' fluid between the inlet and the outlet of the 'process' plate is equal to $Cp_a = 4179$ J/kg/° C. The power received by the 'utility' fluid is therefore: $W = -0.02867 \times 4201 \times (-1.7) = 205$ Watts. The power loss by the 'process' fluid is therefore: $W = 0.00213 \times 4179 \times 23.6 = 210$ Watts. The difference between the two calculated powers is ascribed to the accuracy of the temperature probes and to the flow rate measurements. In this example, the average of the two calculated above i.e. $W = (210+205)/2 = 207.5$ Watts will be taken as the value of the exchanged power.

The average logarithmic temperature is calculated by the relationship indicated above and numerically gives:

$$\Delta T_m I = [23.6 - (-1.7)]/\text{Ln}\,[(69.6 - 9.8)/(46 - 11.5)] = 46°\,\text{C}.$$

From this, it is therefore inferred that: $US = 207.5/46 = 4.51$ W/° C.
Knowing the exchange surface area '5', the heat exchange coefficient 'U' expressed in W/m²/° C. is inferred therefrom.

Within the scope of the method of the invention, it is essential to control the temperature in order to limit the variation of the conversion rate.

The reactions applied within the scope of the present invention are generally exothermic.

Among the catalysts used in the method of the invention, mention may notably be made of the catalysts such as those described in the international application WO 02/53614 or WO 01/49766.

According to a preferred embodiment, the method as defined above comprises the use of a catalyst selected from quaternary ammonium hydroxides of the following formula (I):

wherein:
$R_1$ represents an alkyl group either saturated or not, comprising from 1 to 20 carbon atoms, an aryl group comprising from 6 to 12 carbon atoms, a cycloalkyl group comprising from 5 to 12 carbon atoms or a heterocyclic system with 5 or 6 chain links including a nitrogen atom, an oxygen atom or a sulfur atom, $R_2$, $R_3$ and $R_4$ represent, independently of each other, an alkyl group, either saturated or not, comprising from 1 to 20 carbon atoms, an aryl group comprising from 6 to 12 carbon atoms, said groups $R_2$, $R_3$ and $R_4$ may optionally be substituted with at least one hydroxyl group or one thiol group.

The notion of heat control is essential within the scope of use of these quaternary ammonium hydroxides, which are sensitive to temperature, and this in order to avoid degradation of these catalysts.

The temperature control for the method of the invention is essential in order to be able to control progress of the reaction.

If the temperature in the reactor is less than 65° C., the reaction does not progress fast enough.

When the temperature in the reactor is above 180° C., the reaction becomes too fast and therefore becomes uncontrollable. It is then no longer possible to control the conversion rate related to the progress of the reaction.

With the present invention it is possible to find a compromise between the reaction rate, which has to be fast (from 1 to 3 minutes), and the degradation of the catalyst.

According to an advantageous embodiment, the method of the invention is characterized in that the conversion step is carried out in a reactor of the reactor-plate exchanger type or a multitubular baffled reactor.

For plate reactors, mention may be made of the Alpha Laval technology as described in patent applications FR 2 823 995, US 2004/0109798, FR 2 880 967, WO 02/85511, US 2006/0159600, EP 1 562 699, and that of the Chart and BRH Group with the Marbond™ Hex Reactor technology (as described in applications WO 02/37047 and WO 02/58840).

Among multitubular baffled reactors, mention may be made of the intensified reactors of the FlexReactor type from the BHR Group.

The present invention also relates to a method as defined above, wherein the conversion step is carried out during a dwelling time in the reactor of less than 1 hour, preferably less than 30 minutes, and still preferably less than 10 minutes, and preferentially less than about 3 minutes.

This reduced dwelling time is significant in order to adapt a method of the batch type into a continuous method, and this because of the large number of calories to be removed. If the dwelling time becomes too significant, the advantage of carrying out the method continuously is then lost.

The catalysts have to be adequate in order to have a limited dwelling time.

In terms of productivity, the increase is for example by about a factor 20 relatively to batch methods.

According to an advantageous embodiment, the method of the invention is characterized in that the isocyanate monomer and the catalyst are added into the reactor simultaneously.

Preferably, the method of the invention is characterized in that the isocyanate monomer is selected in the group formed by aliphatic, cycloaliphatic and aromatic isocyanates.

According to a particularly advantageous embodiment of the method as defined above, the isocyanate monomer is selected from the group consisting of 1,6-hexamethylene diisocyanate (HDI), 1,12-dodecane diisocyanate, cyclobutane-1,3-diisocyanate, cyclohexane-1,3 and/or 1,4-diisocyanate, 1-isocyanato-3,3,5-trimethyl-5-isocyanatomethyl cyclohexane (isophorone diisocyanate-IPDI), isocyanatomethyloctylene di-isocyanate (TTI), dicyclohexyl-methane-4,4'-diisocyanate, toluene diisocyanate (TDI), methylene bisphenylisocyanate (MDI), 2,2,4-trimethyl-1,6-hexamethylenediisocyanate, 2,4,4-trimethyl-1,6-hexamethylene diisocyanate (TMDI), 2,4- and/or 2,6-hexahydrotoluoylene di-isocyanate ($H_6$TDI), 2,4- and/or 2,6-toluoylene diisocyanate, hexahydro-1,3 and/or 1,4-phenylene diisocyanate, 2-methylpentamethylene diisocyanate (MPDI), 1,3- and/or 1,4-phenylene diisocyanate, tetramethylxylylene diisocyanates (TMXDI), triphenyl-methane-4,4',4"-triisocyanate, lysine diisocyanate as well as esters of lysine di- or tri-isocyanate (LDI or LTI), diphenyl-methane-2,4' and/or 4,4'-diisocyanate (MDI), perhydro 2,4' and/or 4,4'-diphenylmethane diisocyanate ($H_{12}$MDI), and generally the aromatic amino precursors or perhydrogenated carbamates, bis-isocyanatomethylcyclohexanes (BIC), notably 1,3-BIC and 1,4-BIC, bis-isocyanatomethylnorbornanes (NBDI) and oligomers of MDI or TDI.

The present invention also relates to a method as defined above wherein the catalyst is selected from the group consisting of tetrabutylammonium hydroxide (TBAOH) and N,N,N-trimethyl-N-(2-hydroxyethyl)ammonium hydroxide (choline hydroxide).

According to an advantageous embodiment, the method of the invention is characterized in that the amount of catalyst used is from about 0.01% to about 0.5% by weight relatively to the monomer weight.

The present invention also relates to a method as defined above for preparing hexamethylene diisocyanate trimer (HDT), comprising a conversion step of 1,6-hexamethylene-diisocyanate (HDI) in the presence of N,N,N-trimethyl-N-(2-hydroxyethyl)ammonium.

The present invention also relates to a method as defined above for preparing hexamethylene diisocyanate trimer (HDT) comprising a step for conversion of 1,6-hexamethyl-enediisocyanate (HDI) in the presence of tetrabutylammonium hydroxide.

According to another advantageous embodiment, the method of the invention is a method as defined above wherein the isocyanate monomer contains more than 30 ppm of hydrolyzable chlorine.

These ranges of hydrolyzable chlorine are an additional advantage of the continuous method relatively to the discontinuous method.

Indeed, within the scope of a batch method, a portion of the catalyst is consumed by species of the "hydrolyzable chlorine" type. By "hydrolyzable chlorine", is meant molecules for which chlorine is bound covalently and from which it may released as $Cl^-$. Analysis of the hydrolyzable chlorine level is carried out by action of a water/methanol mixture (2 h, reflux) on the relevant monomer and by determination of the $Cl^-$ concentration by suitable means. The partial consumption of the catalyst by species of the "hydrolyzable chlorine" type is expressed by a delayed reaction onset and a lower yield for an isocyanate containing a Cl concentration of about 120 ppm (see Example 3 hereafter).

Now, the continuous method allows this difference to be erased. It is therefore not necessary, within the scope of the method according to the present invention, to adapt the operating conditions depending on the raw materials used.

EXPERIMENTAL PART

Example 1

Continuous Tests in a Plate Reactor

1—Characteristic of the Reactor:

The plate reactor used is a stainless steel reactor at a laboratory scale with which it is possible to treat flow rates from 200 milliliters par hour to 10 liters per hour. It consists of 3 plates, the structure (splines of a diameter of about 2 mm cut in the plate) of which was designed in order to promote turbulences of the fluid which passes through it and thereby provide optimum heat transfer performances. For this reactor, the performances have been characterized by a heat exchange coefficient (U) of 5,000 Watts per cubic meter and per degree Celsius. The coefficient U was measured as indicated above by using water as a fluid. The three plates positioned in series have an overall volume of 37.01 cm$^3$ and an exchange surface area of 0.074 m$^2$. The specific heat exchange coefficient (US/V) is therefore 8,020 kilowatts per cubic meter and per degree Celsius.

Each of these plates is positioned between two other plates in which the heat transfer fluid flows for removing the calories. Several temperature probes are positioned along the "process" plates (plates receiving the reaction mixture), in order to measure the temperature profile in the reactor during the test.

2—Continuous Tests for Trimerization of HDI by Catalysis with a Quaternary Ammonium:

The tests consisted of feeding the plate reactor by co-addition of hexamethylene diisocyanate (HDI, Rhodia) and of catalyst (45% choline in methanol or 40% tetrabutylammonium hydroxide in methanol, Aldrich) in solution in ethylhexanol (Aldrich).

The plate reactor is brought to the desired work temperature by circulation of the heat transfer fluid in the corresponding plate. The reagents are then fed either with the current or against the current of the heat transfer fluid (notably silicon oil heated to 90° C. beforehand) through the adjacent process plates. Within the scope of the tests described hereafter, the reagents are fed against the current. The conversion of HDI in HDT occurs in the microstructure of the plates and leads to evolvement of heat corresponding to 18 kcal/mol of converted HDI. It is this heat evolvement which should be efficiently and rapidly removed in order to control the chemistry and optimize productivity.

a. Continuous Test of Trimerization of HDI by Choline Catalysis

The evaluation of the heat performances of the plate reactor is carried out in two phases. First of all, it is fed with pure HDI without the catalytic solution and the heat profile along the reactor is measured after stabilization. With this first phase, it is possible to obtain the reference temperature profile in the absence of reaction. The catalystic solution (1.3% by weight of catalyst in ethylhexanol) is then jointly fed and the total flow rate in the reactor, therefore the dwelling time, is adjusted in order to obtain a conversion rate of HDI comprised between 20 and 50%. The reaction is established and, after reaching the stationary operating conditions (stabilized concentration of the products at the outlet of the reactor), the same profile is measured. Both profiles are compared in FIG. 1.

Figure 1:
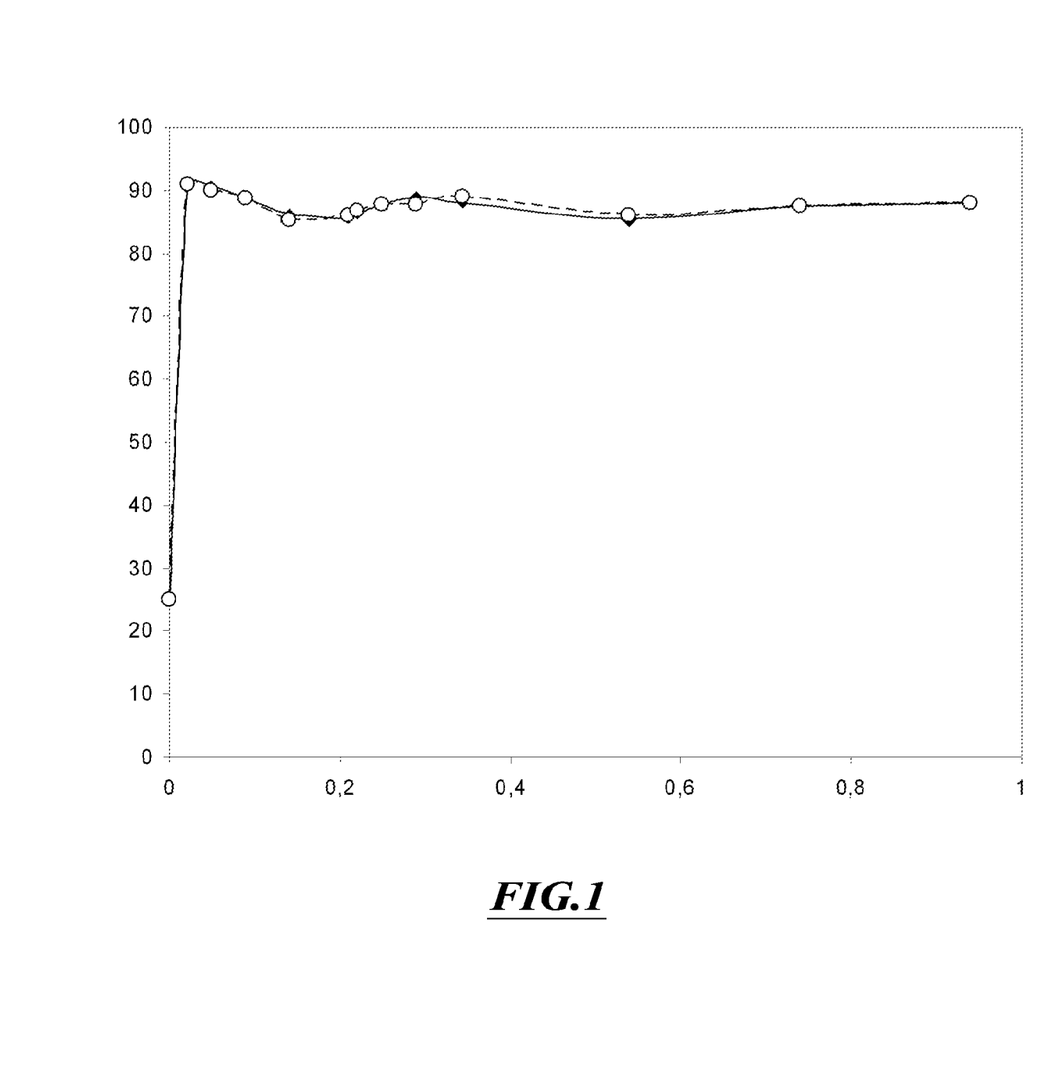
FIG. 1 illustrates the temperature profiles under stationary conditions in the presence of the catalyst (choline) (solid line curve with lozenges) and under stationary conditions without any catalyst (curve in dotted lines with circles). These curves represent the temperature (in ° C.) versus the variable z/L, L corresponding to the total length of the splines of the plates of the reactor and z/L corresponding to the position of the temperature probes along this length. Thus, the value z/L=0 corresponds to the inlet of the reactor and the value z/L=1 corresponds to the outlet of the reactor.

It appears that both temperature profiles are perfectly superposable. This indicates that the heat evolved during the reaction is perfectly removed by the plate reactor. Of course, this is what is expected from this technology but this is particularly important in the case of choline catalysis. Indeed, choline has the characteristic of degrading thermally. A minimum temperature is required in order to have a sufficient reaction rate in order to reach the desired conversion rate for a fixed passage time. But this temperature should not be too high, with the risk of rapidly degrading the catalyst and that it becomes inactive before the reaction reaches this conversion rate; whence the benefit of the plate reactor with which the proper temperature may be imposed, while perfectly removing the calories generated by the reaction.

The table below actually shows the sensitivity of the reagent with the temperature and the effect mentioned above:

| Catalyst | Reactor temperature (° C.) | Catalyst flow rate (ml/mn) | HDI flow rate (kg/h) | choline/HDI (mole %) | Dwelling time (min) | HDI conversion rate (%) |
|---|---|---|---|---|---|---|
| Choline | 97 | 0.204 | 0.6 | 0.065 | 4.4 | 25% |
| Choline | 93 | 0.204 | 0.67 | 0.06 | 3.95 | 35% |
| Choline | 91 | 0.18 | 0.58 | 0.06 | 4.5 | 39% |

It is therefore noticed here that when the temperature increases, the conversion rate decreases, and this is due to the too significant degradation of the catalyst. Controlling the temperature therefore involves controlling the conversion rate.

b. Continuous Test of Trimerization of HDI by Tetrabutylammonium Hydroxide (TBAOH) Catalysis This same plate reactor is tested for trimerization of HDI by using tetrabutylammonium hydroxide (TBAOH) as a catalyst. The catalytic solution used in this test contains 1.3% by weight of TBAOH catalyst in ethylhexanol. This catalyst has the same catalytic properties as choline for the synthesis of HDT from HDI. On the other hand, it is thermally much more stable than choline. Consequently, the catalytic activity of TBAOH is much greater and trimerization kinetics is increased.

This type of catalysis is difficult to control in a batch or semi-batch reactor with a reaction which tends towards thermal runaway.

It is perfectly controlled in the plate reactor. In the table below at 82° C., the impact of the dwelling time in the reactor on the conversion rate is appreciated.

| Catalyst | Reactor temperature (° C.) | Catalyst flow rate (ml/mn) | HDI flow rate (kg/h) | TBAOH/HDI (mole %) | Dwelling time (min) | HDI conversion rate (%) |
|---|---|---|---|---|---|---|
| TBAOH | 82 | 0.218 | 0.540 | 0.03 | 4.9 | 40.9% |
| TBAOH | 82 | 0.224 | 0.620 | 0.027 | 4.3 | 38.7% |
| TBAOH | 82 | 0.224 | 0.630 | 0.027 | 4.25 | 35% |
| TBAOH | 82 | 0.224 | 0.635 | 0.027 | 4.2 | 33% |

If the dwelling time is imposed, the conversion rate may also be controlled by the catalytic load. The table below shows the sensitivity of the chemistry conducted continuously towards the catalytic load:

| Catalyst | Reactor temperature (° C.) | Catalyst flow rate (ml/mn) | HDI flow rate (kg/h) | TBAOH/HDI (mole %) | Dwelling time (min) | HDI conversion rate (%) |
|---|---|---|---|---|---|---|
| TBAOH | 85 | 0.102 | 0.530 | 0.015 | 5.05 | 3.9 |
| TBAOH | 85 | 0.136 | 0.535 | 0.020 | 5 | 24.7 |
| TBAOH | 85 | 0.170 | 0.540 | 0.025 | 4.9 | 39 |

Example 2

Comparative Tests in Batch Reactor

As a comparison, both of these reaction systems (choline/TBAOH) were tested in a stirred glass reactor with a jacket. The reaction is conducted under batch conditions, the reagents are added into the reactor, and the heat transfer fluid which crosses the jacket is gradually brought (temperature ramp) from room temperature up to 85° C. The temperature of the jacket is then maintained at 85° C. until the experiment is stopped.

1—Characteristics of the Reactor:

The glass reactor with a jacket has an inner diameter of 0.08 m (8 cm). The volume of reagents added into this reactor represents about 0.3 l (300 ml) which represents a contact surface area with the wall of about 0.03 $m^2$. The heat transfer coefficient of the glass in contact with an organic solution is given conventionally as about 180 $W.m^{-2}.°C.^{-1}$. The specific heat exchange coefficient (US/V) of the reactor is therefore of about 18 kilowatts per cubic meter and per degree Celsius.

2—Performances in a Batch Reaction:

Operating Conditions:

| Catalyst | Heat transfer fluid temperature | HDI load (g) | Catalytic load (g) | Ethylhexanol load (g) | Catalyst/HDI (mole %) |
|---|---|---|---|---|---|
| Choline | Troom → 85° C. | 316.1 | 0.065 | 2.4372 | 0.03% |
| TBAOH | Troom → 85° C. | 309.8 | 0.142 | 4.925 | 0.03% |

Figure 2:
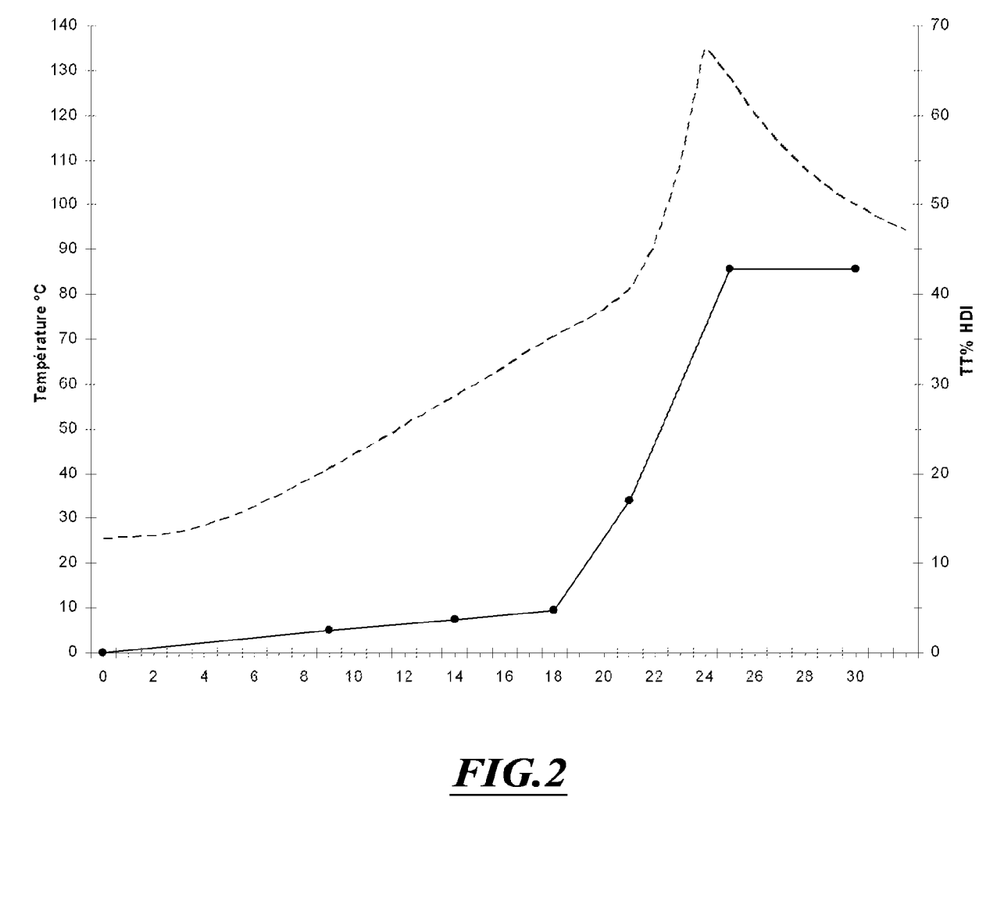
FIG. 2 illustrates the temperature profile under batch conditions in the presence of the catalyst choline. The curve in dotted lines illustrates the change in temperature (° C.) versus time (min) and the solid line curve with the black circles illustrates the conversion rate of HDI (%) versus time (min).
Figure 3:
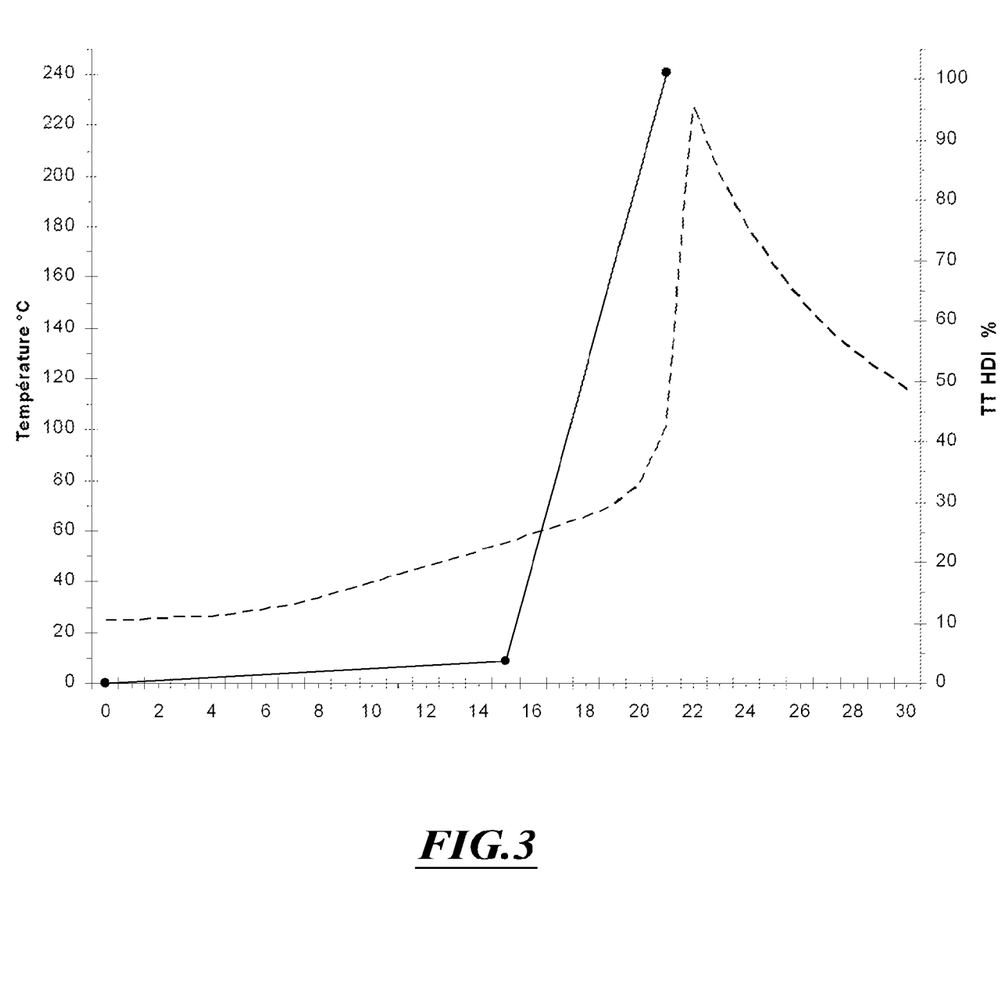
FIG. 3 illustrates the temperature profile under batch conditions in the presence of the catalyst TBAOH. The curve in dotted lines illustrates the change in temperature (° C.) versus time (min) and the solid line curve with the black circles illustrates the conversion rate of HDI (%) versus time (min).

The graphs of FIG. 2 and of FIG. 3 give the temperature profiles of the reaction medium and of that of the HDI conversion.

Two different thermal behaviors are obtained upon considering both of these tests.

Test with choline: The reaction is initiated around 70° C. and the reaction accelerates. The generated heat is not efficiently removed and accumulates in the reaction mixture. This has the effect of raising the temperature of the medium which itself accelerates the reaction again. One is in the presence of thermal runaway which leads the temperature to about 135° C. rapidly. At this temperature, the catalyst is completely thermally destroyed (the conversion suddenly stops), and the reaction medium slowly cools by gradually removing its calories through the jacket.

Test with TBAOH: The reaction is also initiated around 70° C. with the same phenomenon as with choline. Thermal runaway rapidly leads the temperature to about 230° C. At this temperature, the catalyst is still active but HDI conversion is complete. This complete conversion has taken from one to two minutes, and the reaction medium slowly cools by gradually removing its calories through the jacket. Here, the reaction medium is too viscous.

Both of these examples exhibit thermal runaway which could not be controlled by the selected equipment (here the stirred reactor). The extrapolation of this technology will remain very delicate or even impossible in the case of TBAOH catalysis.

Whence the benefit of having tools and equipment which allow perfect monitoring and control of thermics. Monitoring and control are quantified by a high value of their specific heat coefficient which characterizes them. Plate reactors provide this property.

Example 3

Tests on the Impact of Hydrolyzable Chlorine

As a comparison, the choline hydroxide catalytic system was tested in a stirred jacketed glass reactor with two HDI monomers with different hydrolyzable chlorine contents (~25 and 120 ppm expressed as chloride). The reaction is conducted under batch conditions, the monomer is placed in the reactor, and then the heat transfer fluid which crosses the jacket, is brought to 85° C. The temperature of the jacket is then maintained at 85° C. until the experiment is stopped. The catalytic solution (1.3% by weight of choline hydroxide in 2-ethylhexanol) is gradually introduced via a syringe pump into the reaction medium.

The reactor used is identical with the one used in Example 2. The volume of reagents added into this reactor represents about 0.8 to 1 l (1,000 ml), which represents a contact surface area with the wall from 0.04 to 0.05 m². The heat transfer coefficient of the glass in contact with an organic solution is given conventionally as about 180 W.m$^{-2}$.° C.$^{-1}$. The specific heat exchange coefficient (US/V) of the reactor is therefore about 8 to 9 kilowatts per cubic meter and per degree Celsius.

Performances in a Batch Reaction:

Operating Conditions:

| Hydrolyzable Cl content of HDI | Heat transfer fluid temperature | HDI load (g) | C Catalytic solution load with 1.3% by weight of choline hydroxide (g) | Introduction time [min] | Catalyst/HDI (mole %) | Transformation rate (HDI) |
|---|---|---|---|---|---|---|
| 25 ppm Cl | 85° C. | 1,000 g | 8.0 | 60 | 0.014% | 63% |
| 120 ppm Cl | 85° C. | 800 g | 6.4 | 60 | 0.014% | 53% |

Test with a HDI with low hydrolyzable chlorine content: The reaction begins at about 10 min after the beginning of the addition of the catalyst. The heat generated in the first part is not completely removed which raises the temperature of the medium. The cryothermostat compensates and the temperature of the reaction medium drops before the increase in temperature becomes linear, a sign of the accumulation of the catalyst in the reaction medium and of the progress of the reaction. After stopping the flow of catalyst, the reaction stops slowly.

Test with a HDI with high hydrolyzable chlorine content: The reaction begins with a time shift of about 6 minutes relatively to HDI with low chlorine content. The amount of heat generated during this phase is less significant and the temperature increases gradually and smoothly.

Figure 4:
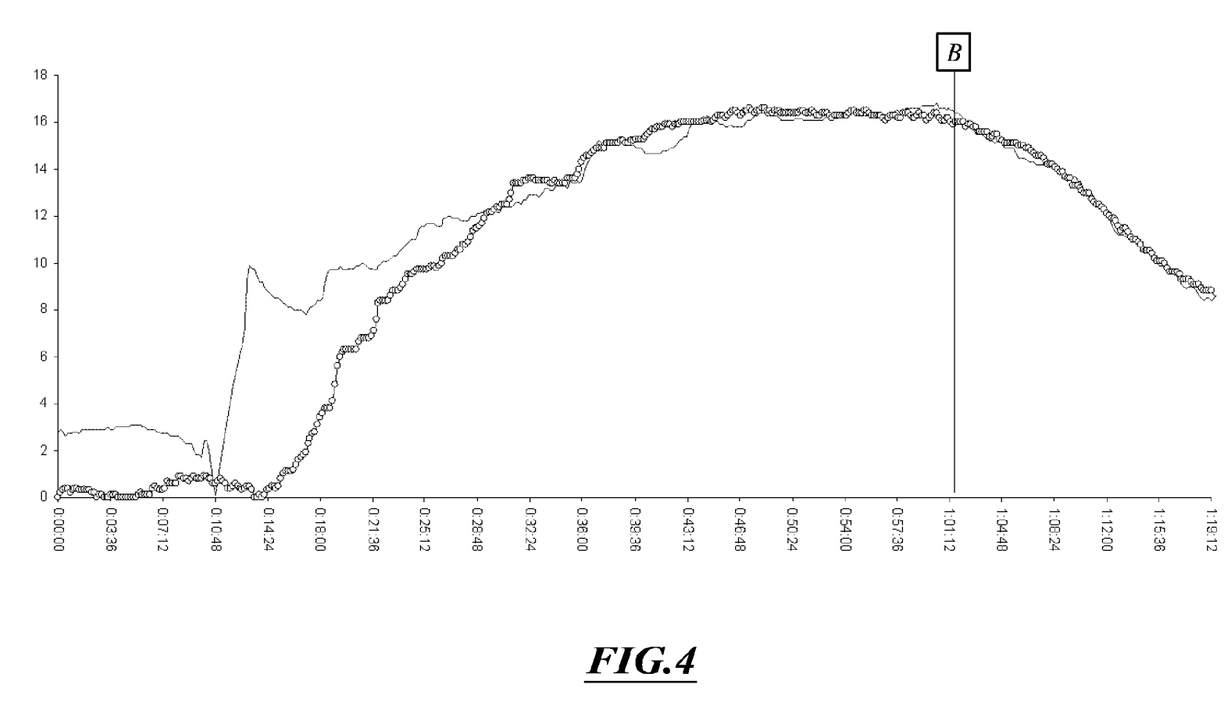
FIG. 4 illustrates the superposition of the temperature profiles of the tests with HDI with a high hydrolyzable chlorine content (curve with the white circles) and with HDI with a low hydrolyzable chlorine content (solid line curve). This figure illustrates the change in temperature ΔT (° C.) versus time (min). "B" indicates the end of the introduction of the catalyst.

The superposition of the two temperature profiles (FIG. 4) shows a more significant catalytic activity of the <<low chlorine content HDI>> test, as soon as the beginning of the reaction, which is confirmed by the greater conversion rate (CR) (63% versus 53%), it being understood that both tests (HDI with low hydrolyzable chlorine content or HDI with high hydrolyzable chlorine content) are carried out under identical conditions and installations.

Within the scope of the present invention, by jointly injecting the HDI monomer and the catalyst, it is possible to operate with an optimum ratio for oligomerization, which, associated with short dwelling time, allows the impact of the hydrolyzable chlorine to be erased. The use of a continuous reactor and more particularly of the reactor described above therefore allows greater flexibility as regards the quality of the raw materials.

The invention claimed is:

1. A method for oligomerization of isocyanates comprising a step for continuous conversion of an isocyanate monomer into a polyisocyanate containing carbamate and/or allophanate groups in the presence of a catalyst, wherein the conversion step is carried out in a plate exchange reactor and at a specific heat exchange coefficient of greater than or equal to about 200 kW/m³/° C.

2. The method as defined by claim 1, wherein the catalyst is selected from quaternary ammonium hydroxides of the following formula (I):

(I)

wherein:
- R₁ is an alkyl group, either saturated or not, comprising from 1 to 20 carbon atoms, an aryl group comprising from 6 to 12 carbon atoms, a cycloalkyl group comprising from 5 to 12 carbon atoms or a heterocyclic system with 5 or 6 chain links including a nitrogen atom, an oxygen atom or a sulfur atom,
- R₂, R₃ and R₄ represent independently of each other an alkyl group, either saturated or not, comprising from 1 to 20 carbon atoms, an aryl group comprising from 6 to 12 carbon atoms, said groups R₂, R₃ and R₄ may optionally be substituted with at least one hydroxyl group or one thiol group.

3. The method as defined by claim 1, wherein the conversion step is carried out during a dwelling time in the reactor of less than one hour.

4. The method as defined by claim 1, wherein the isocyanate monomer and the catalyst are added into the reactor simultaneously.

5. The method as defined by claim 1, wherein the isocyanate monomer is selected from the group consisting of aliphatic, cycloaliphatic and aromatic isocyanates.

6. The method as defined by claim 1, wherein the isocyanate monomer is selected from the group consisting of 1,6-hexamethylene diisocyanate, 1,12-dodecane diisocyanate, cyclobutane-1,3-diisocyanate, cyclohexane-1,3and/or 1,4-diisocyanate, 1-isocyanato-3,3,5-trimethyl-5-isocyanatomethylcyclohexane, isocyanatomethyloctylene-diisocyanates, dicyclohexyl-methane-4,4'-diisocyanate, toluene diisocyanate, methylene bis-phenylisocyanate, 2,2,4-trimethyl-1,6-hexamethylene diisocyanate, 2,4- and/or 2,6-hexahydrotoluylene diisocyanate, 2,4- and/or 2,6-toluylene diisocyanate, hexahydro-1,3 and/or 1,4-phenylene diisocyanate, 2-methyl-pentamethylene diisocyanate, 1,3- and/or 1,4-phenylene diisocyanate, tetramethylxylylene diisocyanates, triphenylmethane-4,4',4"-triisocyanate, lysine diisocyanate, esters of lysine di- or tri-isocyanate, diphenylmethane-2,4' and/or 4,4'-diisocyanate, perhydro 2,4'- and/or 4,4'-diphenylmethane diisocyanate, and generally aromatic amino precursors or perhydrogenated carbamates, bis-isocyanatomethyl-cyclo-hexanes, bis-isocyanato-methyl-norbornanes and oligomers of methylene bis-phenylisocyanate or toluene diisocyanate.

7. The method as defined by claim 1, wherein the catalyst is selected from the group consisting of tetrabutylammonium hydroxide and N,N, N-trimethyl-N-(2-hydroxyethyl) ammonium hydroxide.

8. The method as defined by claim 1, wherein the amount of catalyst used is from about 0.01% to about 0.5% by weight relatively to the monomer weight.

9. The method as defined by claim 1, for preparing a hexamethylene diisocyanate trimer comprising a step for converting 1,6-hexamethylene diisocyanate in the presence of N,N,N-trimethyl-N-(2-hydroxyethyl)ammonium.

10. The method as defined by claim 1, for preparing a hexamethylene diisocyanate trimer comprising a step for converting 1,6-hexamethylene diisocyanate in the presence of tetrabutylammonium hydroxide.

11. The method as defined by claim 1, wherein the isocyanate monomer contains more than 30 ppm of hydrolyzable chlorine.

12. The method as defined by claim 6, wherein the bis-isocyanatomethylcyclo-hexanes comprise 1,3-bis-isocyanatomethylcyclo-hexane and 1,4-bis-isocyanatomethylcyclo-hexane.

\* \* \* \* \*